United States Patent
Kaye et al.

(10) Patent No.: US 9,968,247 B2
(45) Date of Patent: May 15, 2018

(54) CLEANING DEVICE FOR AN ENDOSCOPIC DEVICE

(71) Applicant: United States Endoscopy Group, Inc., Mentor, OH (US)

(72) Inventors: Christopher J. Kaye, Eastlake, OH (US); Gary E. Mann, Mentor, OH (US); Michael Charles Hauser, Chardon, OH (US); Joseph Mrva, Kirtland, OH (US); Kelsey G. Eikens, Mentor, OH (US)

(73) Assignee: UNITED STATES ENDOSCOPY, INC., Mentor, OH (US)

( * ) Notice: Subject to any disclaimer, the term of this patent is extended or adjusted under 35 U.S.C. 154(b) by 73 days.

(21) Appl. No.: 14/703,426

(22) Filed: May 4, 2015

(65) Prior Publication Data

US 2015/0313681 A1    Nov. 5, 2015

Related U.S. Application Data

(60) Provisional application No. 61/987,857, filed on May 2, 2014.

(51) Int. Cl.
| | |
|---|---|
| A61B 1/12 | (2006.01) |
| A61B 90/70 | (2016.01) |
| A61M 25/00 | (2006.01) |

(52) U.S. Cl.
CPC ...... *A61B 1/122* (2013.01); *A46B 2200/3013* (2013.01); *A61B 2090/701* (2016.02); *A61M 2025/0019* (2013.01)

(58) Field of Classification Search
CPC ... A61B 1/122; A61B 2090/701; A61B 90/70; A61M 2025/0019; A46B 2200/3013
See application file for complete search history.

(56) References Cited

U.S. PATENT DOCUMENTS

| | | | |
|---|---|---|---|
| 1,425,435 | A | 8/1922 | Allen |
| 1,711,352 | A | 4/1929 | Jeffreys |
| 2,701,559 | A | 2/1955 | Cooper |
| 2,739,585 | A | 3/1956 | Ayre |
| 2,839,049 | A | 6/1958 | MacLean |
| 2,847,990 | A | 8/1958 | Ayre |
| 2,955,591 | A | 10/1960 | MacLean |
| 3,074,396 | A | 1/1963 | MacLean |

(Continued)

FOREIGN PATENT DOCUMENTS

| | | |
|---|---|---|
| CN | 2198876 | 5/1995 |
| CN | 2281763 | 5/1998 |

(Continued)

OTHER PUBLICATIONS

International Search Report and Written Opinion from PCT/US2015/029082, dated Jul. 23, 2015.

(Continued)

*Primary Examiner* — Laura C Guidotti
(74) *Attorney, Agent, or Firm* — Calfee Halter & Griswold LLP

(57) ABSTRACT

A cleaning device for use with an endoscope. The device includes an elongated and flexible base and a set of discs axially spaced along the base. Each disc is positioned along the base at a center point of the disc. The size and spacing of the discs may vary within the set of discs.

11 Claims, 6 Drawing Sheets

(56) References Cited

U.S. PATENT DOCUMENTS

| | | | |
|---|---|---|---|
| 3,513,830 A | 5/1970 | Kalayjian | |
| 3,613,664 A | 10/1971 | Willson et al. | |
| 3,800,781 A | 4/1974 | Zalucki | |
| 3,881,464 A | 5/1975 | Levene | |
| 4,108,162 A | 8/1978 | Chikashige et al. | |
| 4,136,680 A | 1/1979 | Southworth | |
| 4,227,537 A | 10/1980 | Suciu et al. | |
| 4,235,244 A | 11/1980 | Abele et al. | |
| 4,235,245 A | 11/1980 | Naito | |
| 4,243,049 A | 1/1981 | Goodale et al. | |
| 4,361,948 A | 12/1982 | Omata | |
| 4,465,072 A | 8/1984 | Taheri | |
| 4,700,713 A | 10/1987 | Kist | |
| 4,759,376 A | 7/1988 | Stormby | |
| 4,763,670 A | 8/1988 | Manzo | |
| 4,877,037 A | 10/1989 | Ko et al. | |
| 4,936,312 A | 6/1990 | Tsukagoshi | |
| 4,946,440 A | 8/1990 | Hall | |
| 4,966,162 A | 10/1990 | Wang | |
| 4,981,143 A | 1/1991 | Sakita et al. | |
| 5,022,408 A | 6/1991 | Mohajer | |
| 5,056,529 A | 10/1991 | de Groot | |
| 5,146,928 A | 9/1992 | Esser | |
| 5,201,323 A | 4/1993 | Vermeuien | |
| 5,217,023 A | 6/1993 | Langdon | |
| 5,370,653 A | 12/1994 | Cragg | |
| 5,427,115 A | 6/1995 | Rowland et al. | |
| 5,456,265 A | 10/1995 | Yim | |
| 5,474,075 A | 12/1995 | Goldberg et al. | |
| 5,533,516 A | 7/1996 | Sahatjian | |
| 5,535,756 A | 7/1996 | Parasher | |
| 5,578,018 A | 11/1996 | Rowland et al. | |
| 5,615,439 A | 4/1997 | Bourrelly | |
| 5,681,335 A | 10/1997 | Serra et al. | |
| 5,713,369 A | 2/1998 | Tao et al. | |
| 5,722,423 A | 3/1998 | Lind et al. | |
| 5,738,109 A | 4/1998 | Parasher | |
| 5,792,074 A | 8/1998 | Turkel et al. | |
| 5,876,138 A | 3/1999 | Gueret | |
| 5,882,329 A | 3/1999 | Patterson et al. | |
| 5,899,850 A | 5/1999 | Ouchi | |
| 5,902,263 A | 5/1999 | Patterson et al. | |
| 5,941,869 A | 8/1999 | Patterson et al. | |
| 6,022,363 A | 2/2000 | Walker et al. | |
| 6,030,397 A | 2/2000 | Monetti et al. | |
| 6,066,152 A | 5/2000 | Strauss et al. | |
| 6,193,674 B1 | 4/2001 | Zwart | |
| 6,258,044 B1 | 7/2001 | Lonky et al. | |
| 6,297,044 B1 | 10/2001 | Eisen et al. | |
| 6,319,242 B1 | 11/2001 | Patterson et al. | |
| 6,336,905 B1 | 1/2002 | Colaianni | |
| 6,494,845 B2 | 12/2002 | Rutenberg | |
| 6,676,609 B1 | 1/2004 | Rutenberg et al. | |
| 6,699,331 B1* | 3/2004 | Kritzler | A61B 17/221 |
| | | | 134/22.11 |
| 7,004,913 B1 | 2/2006 | Rutenberg et al. | |
| 7,108,661 B2 | 9/2006 | Secrest et al. | |
| 7,416,555 B2 | 8/2008 | Krivoruchko | |
| 7,722,613 B2 | 5/2010 | Sutterlin et al. | |
| 8,256,057 B2 | 9/2012 | Galantai et al. | |
| 8,490,235 B2* | 7/2013 | Soetermans | A46B 15/0055 |
| | | | 15/104.05 |
| 8,566,995 B2* | 10/2013 | Asano | A61B 1/122 |
| | | | 15/104.05 |
| 8,968,213 B2 | 3/2015 | Roush et al. | |
| 2001/0046406 A1 | 11/2001 | Schrepf | |
| 2004/0260199 A1 | 12/2004 | Hardia, Jr. et al. | |
| 2005/0256426 A1 | 11/2005 | Brugge | |
| 2006/0162105 A1 | 7/2006 | Abe | |
| 2006/0202387 A1 | 9/2006 | Jean-Paul | |
| 2006/0287667 A1 | 12/2006 | Abele | |
| 2009/0049627 A1 | 2/2009 | Kritzler | |
| 2009/0306702 A1 | 12/2009 | Miloslavski et al. | |
| 2009/0326414 A1 | 12/2009 | Peltier | |
| 2010/0065083 A1 | 3/2010 | Soetermans | |
| 2010/0139018 A1 | 6/2010 | Herbert | |
| 2010/0234848 A1 | 9/2010 | Sutterlin et al. | |
| 2010/0307223 A1 | 12/2010 | Jeftic-Stojanovski et al. | |
| 2011/0028787 A1 | 2/2011 | Tabuchi | |

FOREIGN PATENT DOCUMENTS

| | | |
|---|---|---|
| DE | 19637144 | 3/1998 |
| DE | 202009006908 U1 | 10/2010 |
| EP | 31228 | 7/1981 |
| ES | 273636 | 1/1984 |
| JP | 07-178099 | 7/1985 |
| JP | 10-272089 | 10/1998 |
| SE | 8903019 | 9/1989 |
| WO | 94/03111 | 2/1994 |
| WO | 12/054480 | 4/2012 |

OTHER PUBLICATIONS

Medivators, "Pull Thru™ Cleaning Device," www.medivators.com/products/endoscope-reprocessing/pre-cleaning/pull-thru, retrieved Jul. 30, 2015.

International Search Report and Written Opinion from PCT/US11/56711 dated Jun. 21, 2012.

Boon, Mathilde E. et al., Exploiting the "Toothpick Effect" of the Cytobrush by Plastic Embedding of Cervical Samples, The International Academy of Cytology, Jan.-Feb. 1991, pp. 57-63, Science Printers and Publishers, St. Louis MO.

Cook Medical, Endoscopy, Cytomax II Double Lumen Biliary Cytology Brush, 2 pgs., printed from the world-wide-web on Sep. 30, 2009, www.cookmedical.com.

Cook Medical, Endoscopy, Howell Biliary Introducer Brush, 2 pgs. Printed from the world-wide-web on Sep. 30, 2009, www.cookmedical.com.

Lonky, Neal et al., Comparison of Standard Papanicolaou Smears and Directed Cytologic Sampling Guided by Speculoscopy, International Journal of Gynecology & Obstetrics, XIV World Congress of Gynecology and Obstetrics (FIGO) 1994, Society of Obstetricians and Gynecologists of Canada.

Cover letter, trademark application for the mark SPIRABRUSH CX, signed Declaration and Power of Attorney, photograph of the submitted "SpiraBrush" sample, First Used in Interstate Commerce Dec. 4, 1992.

Restriction Requirement from U.S. Appl. No. 13/276,028 dated May 8, 2013.

Response to Restriction Requirement from U.S. Appl. No. 13/276,028 dated Jun. 10, 2013.

Office Action from U.S. Appl. No. 13/276,028 dated Jul. 17, 2013.
Response to Office Action from U.S. Appl. No. 13/276,028 dated Jan. 17, 2014.

Office Action from U.S. Appl. No. 13/276,028 dated Feb. 14, 2014.
Amendment from U.S. Appl. No. 13/276,028 dated Aug. 1, 2014.
Notice of Allowance from U.S. Appl. No. 13/276,028 dated Oct. 28, 2014.

European Search Report from Application No. 15786228.5 dated Dec. 1, 2017.

* cited by examiner

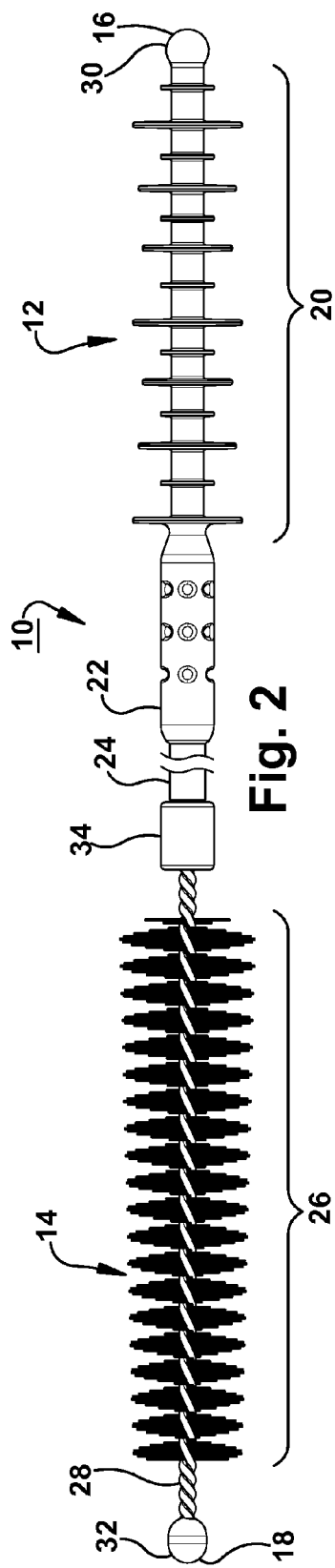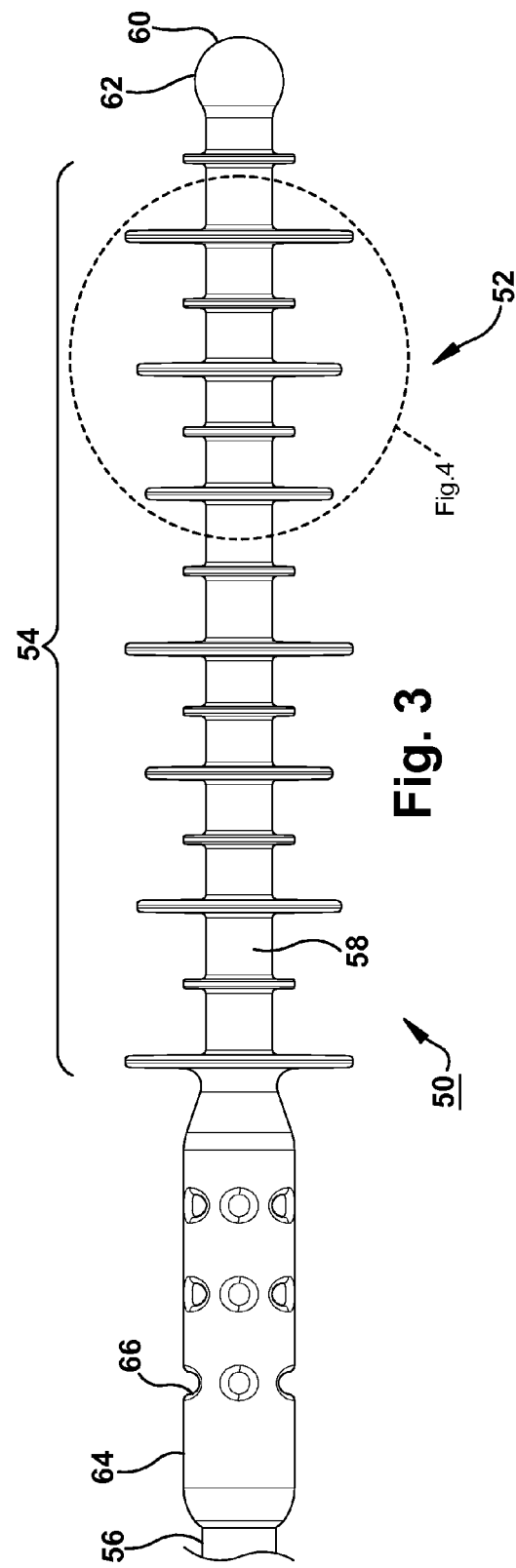

CLEANING DEVICE FOR AN ENDOSCOPIC DEVICE

CROSS-REFERENCE TO RELATED APPLICATION

This application claims the benefit of and priority to U.S. Provisional Patent Application Ser. No. 61/987,857, entitled CLEANING DEVICE FOR AN ENDOSCOPIC DEVICE and filed May 2, 2014, the entire disclosure of which is incorporated herein by reference, to the extent that it is not conflicting with the present application.

BACKGROUND

Endoscopic devices are well-known in the medical arts and are commonly used for numerous medical procedures. One exemplary procedure is removing polyps, lesions or other types of targeted tissue from the gastrointestinal wall of a human subject. During this and other endoscopic procedures, the exterior and interior portions of the endoscope are typically contaminated. Devices which decontaminate the endoscope can help to sterilize the endoscope for future procedures as well as lengthen the life of the endoscope.

SUMMARY

The present application describes a cleaning device for use to clean interior and exterior portions of an endoscopic device.

The cleaning device includes an elongated and flexible base, and a set of discs axially spaced along the base. The individual discs may have a different size or relative spacing to another disc in the set of discs.

Further features and advantages of the invention will become apparent from the following detailed description made with reference to the accompanying drawings.

BRIEF DESCRIPTION OF THE DRAWINGS

Features and advantages of the general inventive concepts will become apparent from the following detailed description made with reference to the accompanying drawings.

FIG. 2 is a side view of the cleaning device of FIG. 1;

FIG. 3 is a side view of another cleaning device with a squeegee component at a distal end;

DETAILED DESCRIPTION

Figure 1:
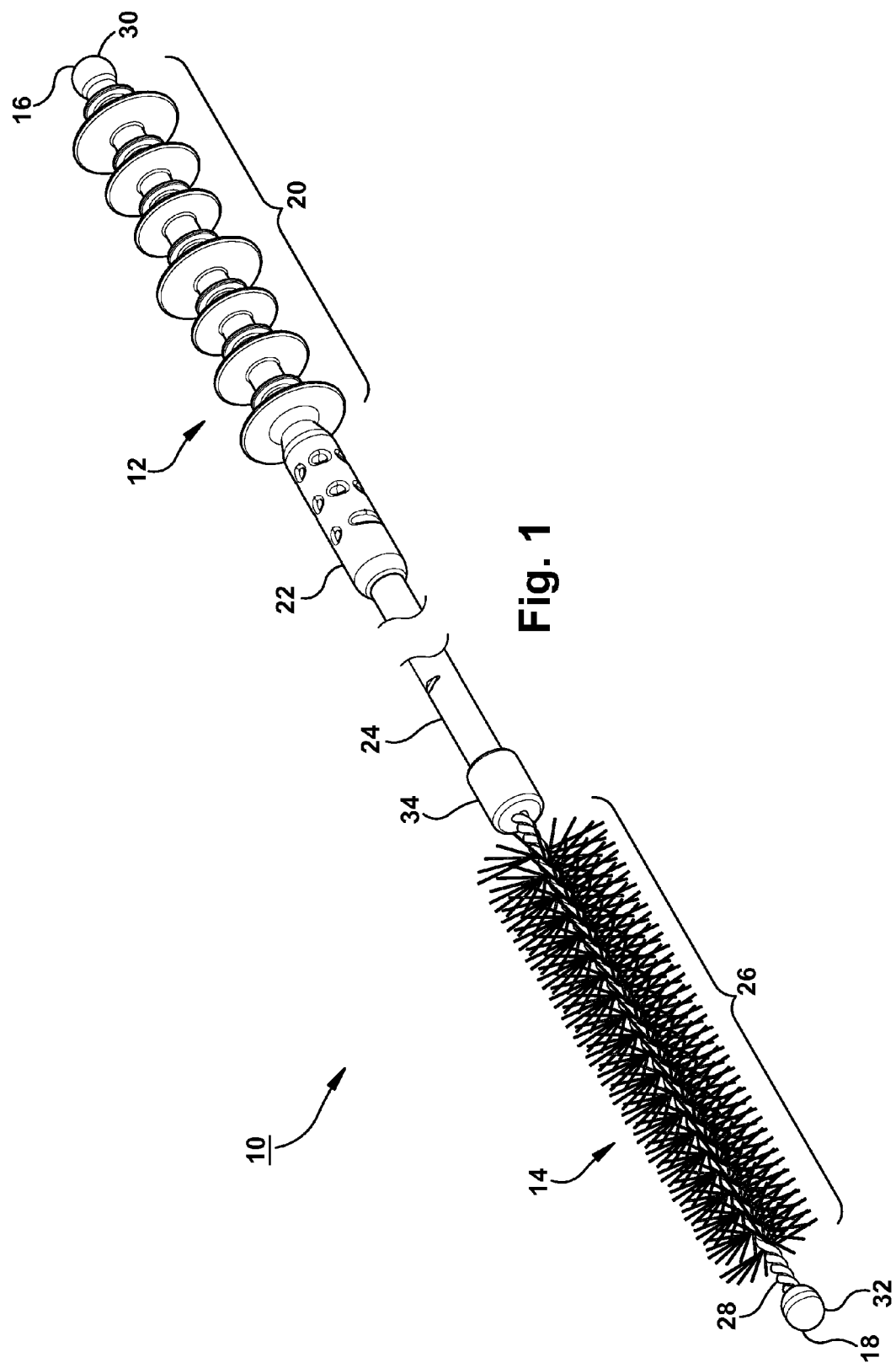
FIG. 1 is a perspective view of a cleaning device with a squeegee component on one end and a brush component on an opposite end.

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

In discussing the invention, the terms "proximal" and "distal" are often used. These terms are used to describe a position or a direction with reference to the operator of the device. For example, the proximal position or proximal direction is toward the user or operator of the device, and the distal position or direction is away from the user or operator of the device, i.e., position or direction toward the endoscope.

Disclosed herein is a cleaning device for an endoscopic device. After a medical procedure using an endoscope or similar device, the device is often soiled and typically requires cleaning and sterilizing. One step in the cleaning and sterilizing process is the use of a cleaning device. One type of cleaning device can be used to clean an endoscopic device by pulling the cleaning device through an instrument channel of the endoscopic device, or inserting and withdrawing the cleaning device from an instrument port of the endoscopic device in a repetitive pattern. The cleaning device may contain one or more cleaning components which may contact surfaces within an endoscopic device, thereby facilitating the removal of contaminants left thereon. Exemplary cleaning components include one or more squeegee components and one or more brush components. A squeegee component may include a set of discs that are spaced along an elongated base, such as a catheter, a twisted wire, a sheath, or a combination thereof.

The discs are made of flexible material. During use of the cleaning device, the set of discs may bend in a direction opposite the direction of movement of the cleaning device. The set of discs collectively act as a squeegee to clean the endoscopic device.

The present disclosure is directed to a cleaning device for an endoscopic device. In one embodiment, the cleaning device includes an elongated and flexible base, and a set of discs axially spaced along the base. Each disc is positioned along the base at a center point of the disc. At least one disc of the set of discs has a circumference which is not equal to a circumference of an adjacent disc of the set of discs.

In another embodiment, the cleaning device includes a catheter, and a set of discs axially spaced along the catheter. Each disc is secured to the catheter at a center point of the disc. At least one disc of the set of discs has a maximum radial distance from the catheter which is greater than an axial distance to an adjacent disc of the set of discs.

In another embodiment, the cleaning device includes a catheter having a proximal end and a distal end, and a squeegee component secured to the catheter. The squeegee component has a sheath and a set of circular discs axially spaced along the sheath. Each disc is positioned on the sheath at a center point of the disc. Each disc of the set of discs has a maximum radial distance from the catheter which is not equal to a maximum radial distance from the catheter of an adjacent disc of the set of discs.

Referring now to the drawings, FIG. 1 is a perspective view of an exemplary cleaning device 10. The cleaning device is a so-called combination device with two types of cleaning components. The cleaning device includes a squeegee component 12 with a set of discs 20 on a first end 16 and a brush component 14 with multiple bristles 26 on an opposite, second end 18. The cleaning device may be of any desired and functional length. As discussed, the squeegee component 12 includes a set of discs. Other exemplary cleaning devices having the same or a similar set of discs are discussed herein. The squeegee component 12 is positioned along an elongated and flexible base 24. The elongated and flexible base may be a hollow tube, such as a catheter, or may be a twisted wire 28 covered along portions of its length by a plastic coating (see FIG. 5). It should be understood by one skilled in the art that the invention may be practiced using a variety of known materials for the base.

The squeegee component generally refers to a cleaning component having cylindrical base and a set of discs. The squeegee component is referred to as the squeegee component, and often, as the squeegee in this specification.

A side view of cleaning device 10 in shown in FIG. 2. The cleaning device 10 includes several other features. A strengthening element 22 is positioned over the elongated base 24. The strengthening element 22 may be a part of the over molding of a sheath to which the set of discs may be secured. Several movement prohibiting structures are included on the device. The first end 16 includes a first ball 30 and the second end 18 includes a second ball 32. Each ball 30, 32 prohibits entry of the cleaning device into undersized and undesired channels and ports in which damage may occur by use of the cleaning device. A cylindrical stop 34 is positioned behind the brush to prohibit entry beyond this point in predetermined sized channels and ports. In use of the cleaning device 10, an operator may use the brush 14 to brush away solid contaminants present in an endoscopic device. By continuing to pull the cleaning device through the endoscope, the squeegee may then be used in a second cleaning step.

The strengthening element will now be generally discussed. In some embodiments, the squeegee component is associated with the catheter through an intermediate surface. In some embodiments, the intermediate surface is used to improve the stiffness of the squeegee component. In some embodiments, a strengthener which is positioned along the catheter serves as the intermediate surface. The strengthener may be associated with the catheter and the squeegee component using any securing mechanism known in the art so long as the securing mechanism maintains the association of the strengthener with the squeegee component and the catheter while cleaning an endoscopic device. In some embodiments, the strengthener is secured to the catheter through a clasp, and the squeegee component is secured to the strengthener by molding the squeegee component to the strengther.

The sheath will now be generally discussed. A sheath may be secured to the catheter, with the set of discs axially spaced along the sheath. As such, each disc of the set of discs is secured to a sheath, and may be manufactured as part of the sheath. An overmold process may allow for a spatial relationship between the sheath and the catheter. By attaching the sheath only at the distal end, a length of the sheath is movable in the proximal direction relative to the base, including the proximal end of the sheath is movable relative to the base.

A cleaning device may have a single cleaning component. FIG. 3 shows an exemplary cleaning device 50 having a catheter 56 and a squeegee 52, which is positioned along the catheter 56. A distal ball 62 is at the distal end 60 of the cleaning device 50. The catheter 56 provides an elongated and flexible base for attachment of the squeegee 52. The attachment may be made by any mechanism known in the art that directly associates the squeegee 52 and the catheter 56 and maintains that association while the cleaning device 50 is being used to clean an endoscopic device. In some embodiments, this attachment occurs by molding the squeegee to the catheter 56 by forming a sheath 58. The attachment of the sheath 58 to the catheter 56 may be done at only a point near the distal end 60 of the cleaning device. As discussed herein, this attachment method allows for relative movement of a length of the sheath relative to the catheter during cleaning.

Referring generally to the catheter, the catheter can be of any proportions, including length, inner diameter, and outer diameter, to efficiently clean endoscopic devices. A catheter used for a pull-through cleaning device generally has a proximal end and a distal end, and multiple component cleaning devices are constructed, relative to the distal end.

In some embodiments, the catheter is between about 80 inches and about 120 inches in length, including about 85 inches in length, about 90 inches in length, and including about 95 inches in length. In some embodiments, the catheter has an inner diameter of about 0.010 inches to about 0.030 inches, including about 0.015 inches, about 0.020 inches, and about 0.025 inches. In some embodiments, the catheter has an outer diameter of about 0.050 inches to about 0.080 inches, including about 0.055 inches, about 0.060 inches, about 0.065 inches, about 0.070 inches, and about 0.075 inches.

A strengthening element is shown in FIG. 3. The strengthening element 64 is positioned along the catheter 56 and in a proximal orientation from the squeegee 52. The strengthening element 64 has a series of apertures 66 around its outside surface.

The squeegee will now be discussed in detail. The squeegee 52 has a set of discs 54. The shape, size and spacing of the discs is discussed herein and illustrated in detail in FIG. 4, which is an enlarged view of the designated circular area of FIG. 3, and shows 5 exemplary discs of the set of discs.

Figure 4:
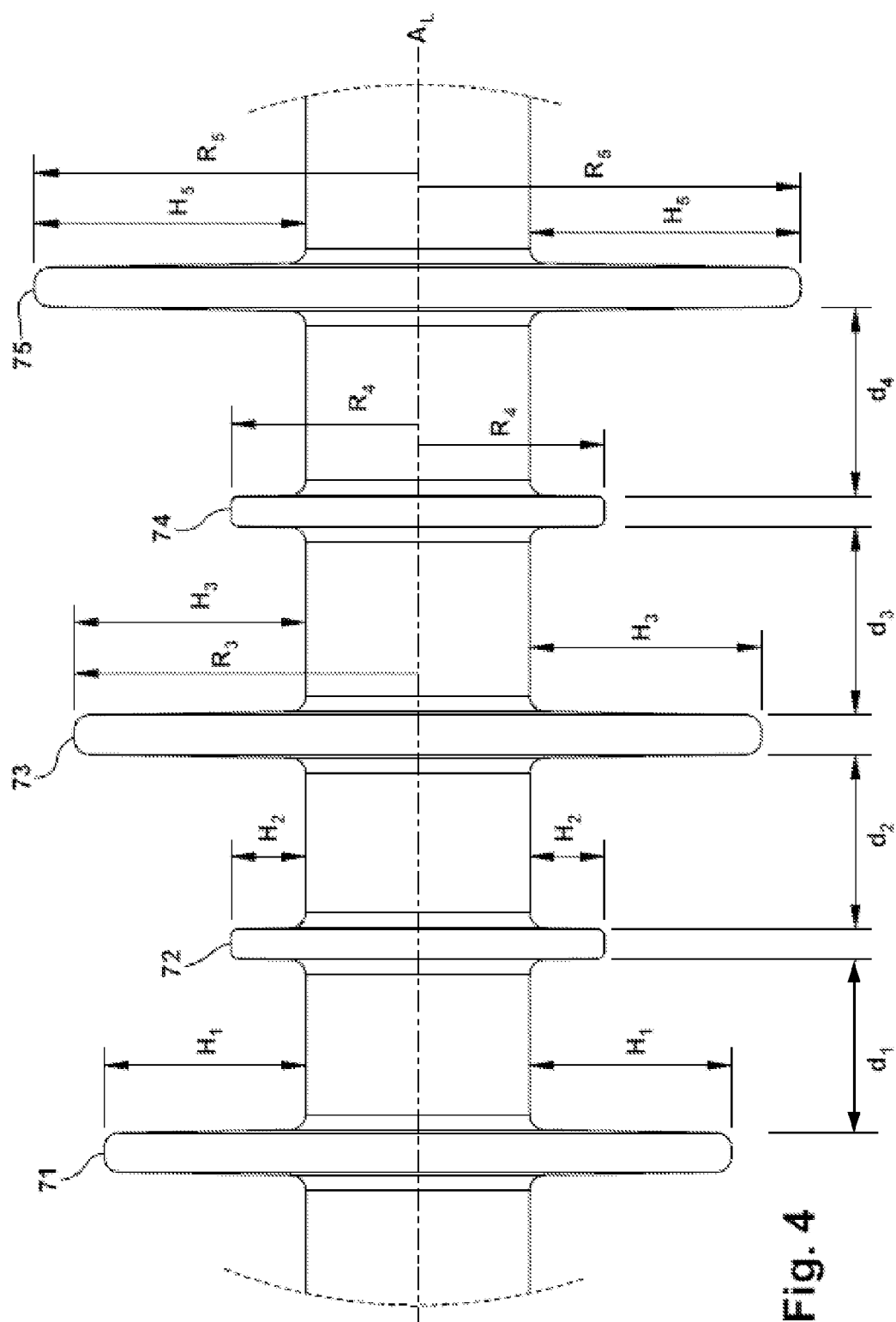
FIG. 4 is an enlarged view of the designated circular area of FIG. 3.

The size, shape and spacing of the discs within the set may vary. FIGS. 3 and 4 illustrate one exemplary set of discs which will now be discussed in detail. However, one skilled in the art will appreciate that the invention may be practiced with a set of discs with vary in size, shape, and spacing from the set illustrated in FIGS. 3 and 4.

Still referring to FIGS. 3 and 4, the set of discs 54 are axially spaced along the catheter 56. Each disc is positioned along the catheter such that center point of each disc is positioned at the longitudinal axis $A_L$ of the catheter, as best shown in FIG. 4.

Specific inventive structural features of the set of discs relating to the size, shape and spacing of discs will now be discussed. In the discussion, the five exemplary discs 71, 72, 73, 74, 75 shown in FIG. 4 of the set of discs 54 will be discussed. Various dimensions are indicated in the figure, including radius of a disc, height of a discs from the catheter outer surface, and axial distance between discs. Each disc is circular shaped. As shown, at least one disc of the set of discs has a circumference which is not equal to a circumference of an adjacent disc of the set of discs. For example, the radius $R_5$ of disc 75 is larger than the radius $R_4$ of adjacent disc 74. Thus, with the discs being circle-shaped, the circumference of disc 75 is larger than the circumference of disc 74.

The set of discs 54 have other inventive structural features. An axial length between any two adjacent discs of the set of discs is less than the maximum radial distance from the base of at least one of the two adjacent discs of the set of discs. For example, the distance $d_4$ between two discs 75, 74 is less than the height $H_5$ of the disc 75 from the base. In this case, the outer diameter of the base is determined by the sheath over the catheter. With this structural arrangement, the disc 75 may touch the disc 74 under certain operational conditions.

Another inventive feature of the set of discs is structural properties of the adjacent discs. As shown, at least one disc of the set of discs has a maximum radial distance from the base which is not equal to a maximum radial distance from the base of an adjacent disc of the set of discs. For example, disc 71 has a maximum radial distance $H_1$ from the base which is not equal to the maximum radial distance $H_2$ from the base of adjacent disc 72. The same trait is true of the next distal pair of disc 72,73, and the following distal pair of discs 73, 74 and the most distal pair 74, 75. The opposite measurement is also true. In other words, at least one disc of the set of discs has a minimum radial distance from the base which is not equal to a minimum radial distance from the base of an adjacent disc of the set of discs. For example, disc 71 has a minimum radial distance $H_1$ from the base which is not equal to the minimum radial distance $H_2$ from the base of adjacent disc 72. The same trait is true of the next distal pair of disc 72,73, and the following distal pair of discs 73, 74 and the most distal pair 74, 75.

Another inventive feature of the set of discs is directed to the radius of the discs. As shown, at least one disc of the set of discs has a radius which is greater than a radius of any adjacent disc of the set of discs. For example, the radius $R_5$ of disc 75 is larger than the radius $R_4$ of adjacent disc 74.

The size of the squeegee itself may vary in the practice of this invention, and is dependent on the number of discs and the axial thickness of each disc. Generally, the squeegee may be of any length to efficiently clean an endoscopic device. In some embodiments, the squeegee component is between about 0.5 inches and 2 inches in length, including about 0.75 inches in length, about 1 inch in length, about 1.25 inches in length, about 1.5 inches in length, and about 1.75 inches in length.

As discussed herein, the squeegee component includes multiple discs. The multiple discs are sized and spaced to efficiently clean the endoscopic device. Unexpectant results regarding improved cleaning efficiency have been found by changing sizing and spacing of the multiple discs such that the at least two discs remain in contact with one another when the squeegee component is within an endoscopic device. Thus, in some embodiments, the multiple discs are sized and spaced as part of the squeegee component such that there is limited space to no space between the multiple discs when the squeegee component is within an endoscopic device.

As shown in the Figures, consecutive discs are differentially sized. In more specific embodiments, sizing of consecutive discs alternates between larger and smaller sized discs. In an even more specific embodiment, a repeating twelve disc mirror pattern is used beginning from the seventh disc ((or example, discs five and nine are of the same size) where the odd-numbered discs are of a larger size than the even-numbered discs, and the odd-numbered discs are progressively larger the greater the distance from middle disc. The discs may be of any absolute size that provides for appropriate proportionality in size between discs as described herein, and of any spacing that maintains contact between consecutive discs when the squeegee component is within an endoscopic device.

The multiple discs may be of any shape or form that cleans the endoscopic device. Exemplary, non-limiting shapes include circular, ovular, and rectangular. In particular embodiments, the multiple discs have a circular shape. In some embodiments, individual discs are of a size between about 1.5 mm and 6.5 mm including about 2.0 mm, about 2.5 mm, about 3.0 mm, about 3.5 mm, about 4.0 mm, about 4.5 mm, about 5.0 mm, about 5.5 mm, and about 6.0 mm.

In some embodiments, spacing between discs is varied to complement the varied disc size. Thus, in some embodiments, spacing between a first even-numbered disc and its odd-numbered disc neighbors is the same, and spacing between the odd-numbered disc neighbors and the next even-numbered disc is different than the spacing between the odd-numbered disc neighbor and the first even-numbered disc.

Now referring generally to multiple component features of the device, certain embodiments of the invention are combination devices. Any component that can facilitate cleaning of an endoscopic device and that can be used in conjunction with the cleaning device disclosed herein, may be combined with the squeegee component for cleaning an endoscopic device. In some embodiments, a component used in combination with the squeegee component is one that complements the function of the squeegee component in cleaning the endoscopic device. The use of complementary cleaning components is expected to provide greater cleaning efficiency than would be expected based on the individual contributions of the cleaning components. For example, an exemplary combined cleaning device is produced by adding a brush component to a squeegee component. The brush component complements the function of the squeegee component because each component enhances the effects achieved by the other component. The brush component can brush away solid contaminants present in an endoscopic device, and the squeegee component can facilitate the cleaning of an endoscopic device by facilitating the removal of matter that is brushed from surfaces of the endoscopic device. Contaminants left in an endoscopic device are more easily brushed away using the brush component due to the actions of the squeegee component in removing material brushed off of the endoscopic device surfaces. Likewise, removal of contaminants by the squeegee component is more efficient when solid material is initially brushed off of the surfaces by the brush component. A brush component and squeegee component may be on opposite ends of an elongated base. Further, the two components can be placed in the same orientation with respect to each other and at the same end of the elongated base. For example, the brush component and the squeegee component may face the same direction and be at the same end of the elongated base.

Figure 5:
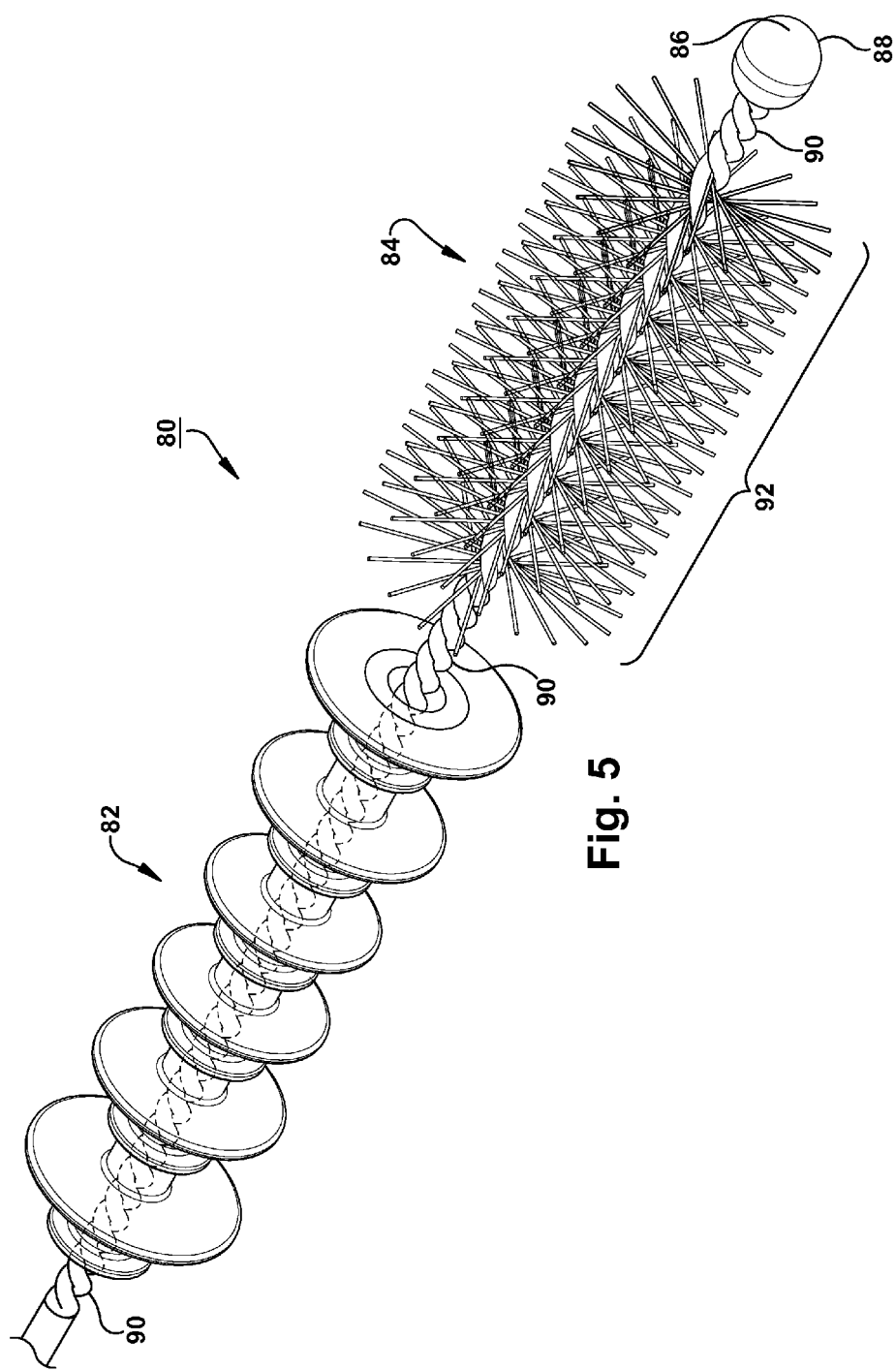
FIG. 5 is a perspective view of another cleaning device with a brush component and a squeegee component on a distal end.

Referring now to FIG. 5, a perspective view of another cleaning device is illustrated. The cleaning device 80 is a multiple component device with a brush 84 and a squeegee 82, each component positioned on a distal end 86 of the device. The brush 84 is positioned on the distal side of the squeegee 82, such that in use, the brush will loosen debris in an area of the endoscope prior to impact of the area with the squeegee 82. The device also includes a distal end ball 88.

A brush component is advantageous for several purposes. Where present, the brush component may be in any proportions and be made of any material that removes debris from an endoscopic device. In some embodiments, the brush component is about 0.5 inches to about 2.5 inches, including about 0.75 inches, about 1 inch, about 1.25 inches, about 1.5 inches, about 1.75 inches, about 2 inches, and about 2.25 inches in length. In some embodiments, the brush component is about 0.2 inches to about 0.3 inches in width, including about 0.21 inches, about 0.22 inches, about 0.23 inches, about 0.24 inches, about 0.25 inches, about 0.26 inches, about 0.27 inches, about 0.28 inches, and about 0.29 inches. It is preferred that the brush component be made of material that allows for some flexibility while the brush component is passed through an endoscopic device.

An exemplary brush component is shown in FIG. 5. The brush 84 contains multiple bristles 92 for contacting debris within an endoscopic device. The bristles 92 can be made of any suitable material known in the art. In some embodiments, the bristles 92 are made of a nylon. In some embodiments, the bristles 92 are placed on a twisted wire, or an overtwist 90. The overtwist 90 can be made of any suitable material known in the art. In some embodiments, the overtwist 90 is made of stainless steel. In some embodiments, the brush component also includes an end ball 88. It should be understood by one skilled in the art that other types of brushes may be used in the practice of this invention besides multiple bristles brushes, such as for example, a sponge, a molded bristle brush, a wire-wound brush, or any brush construction known in the art for contacting debris within a narrow passage, such as for example, an endoscope channel.

In the cleaning device 80 shown in FIG. 5, the brush and the squeegee are attached to the same twisted wire 90. In an assembly option, the squeegee may be over-molded over the twisted wire 90. A wire has some benefits over a catheter. This technique allows the squeegee discs to fill completely and prohibits the elastomer from stretching and tearing as a result of friction from squeegee/endoscope channel interface. Further, the wire ensures adequate stiffness/link resistance as opposed to a thin-walled catheter. Wire can be stripped at a distal end and twisted bristle brush would be welded to create attachment of a brush component. However, one skilled in the art will appreciate the invention may be practiced with any suitable elongated and flexible base, such as plastic tubing, or other catheter stock.

If a catheter is used as the elongated base, several advantageous assembly techniques may be used. The catheter outer diameter may be reduced at proximal end where the squeegee discs will be over-molded to ensure material flow to fill geometry. This reduction also prohibits the elastomer section from stretching and breaking due to friction from squeegee/endoscope channel interface. Further, the catheter outer diameter reduction, or notch cutouts, i.e., "compressed sections" at a proximal end where the squeegee discs will be over-molded, will ensure material flow to fill geometry and create a mechanical interlock to the catheter. This reduction also prohibits the elastomer section from stretching and breaking due to friction from squeegee/endoscope channel interface.

Figure 6:
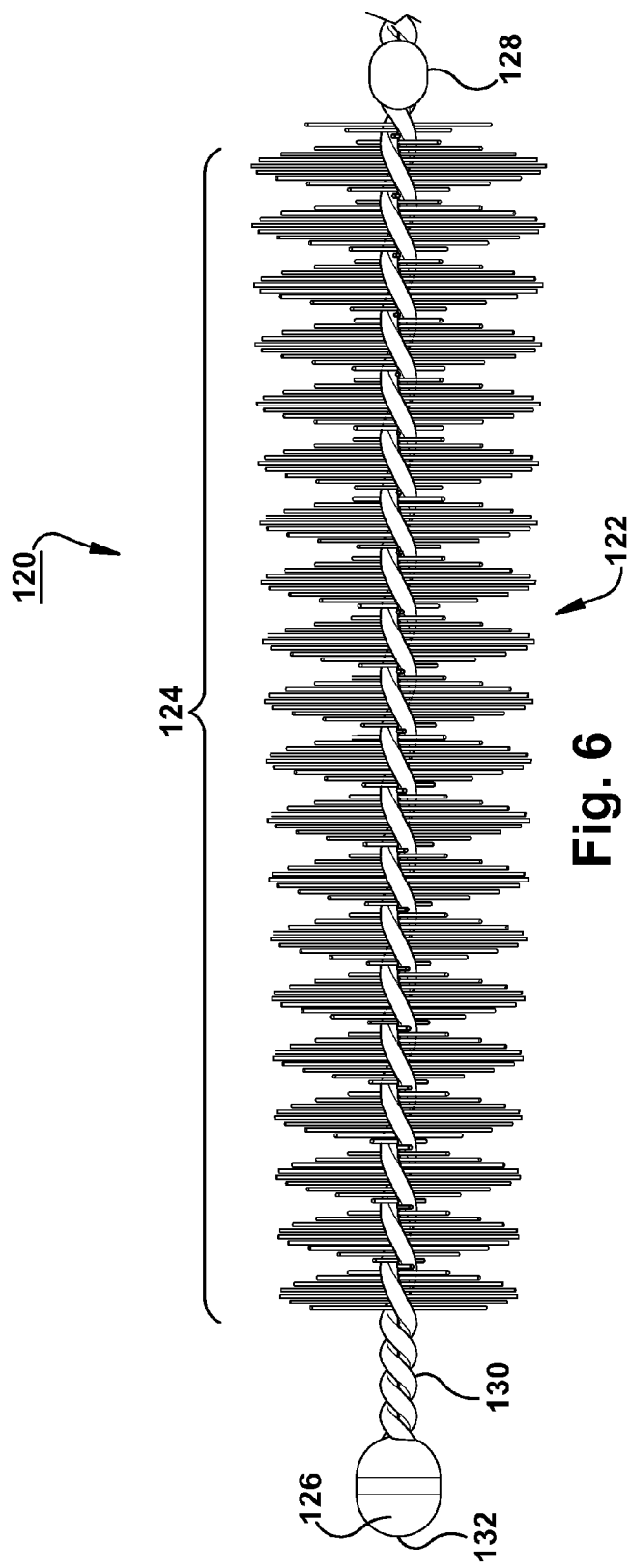
FIG. 6 is a perspective view of a portion of another cleaning device, showing only a brush component on a distal end.

As discussed herein, another exemplary cleaning device is shown in FIG. 6. This device 120 includes a mechanical barrier for limiting insertion depth of the cleaning device into an endoscopic device. FIG. 6 shows a perspective view of a portion of the cleaning device 120. Only a brush component is shown on the distal end 132 of the device. The brush 122 includes multiple bristles 124 attached to a twisted wire 130. A distal stop ball 126 is on the distal side 132 of the brush 122 and a proximal stop ball 128 is on the proximal side of the brush 122 and the distal side of the squeegee (not shown).

The mechanical stop may be in any practical shape, such as a ball, a cylinder or cube shape. The stop may be injection molded onto a twist wire at a position distal or proximal from a squeegee. The stop may also be formed by acrylic casting and manually slid onto the wire or catheter and glued in place.

Figure 7:
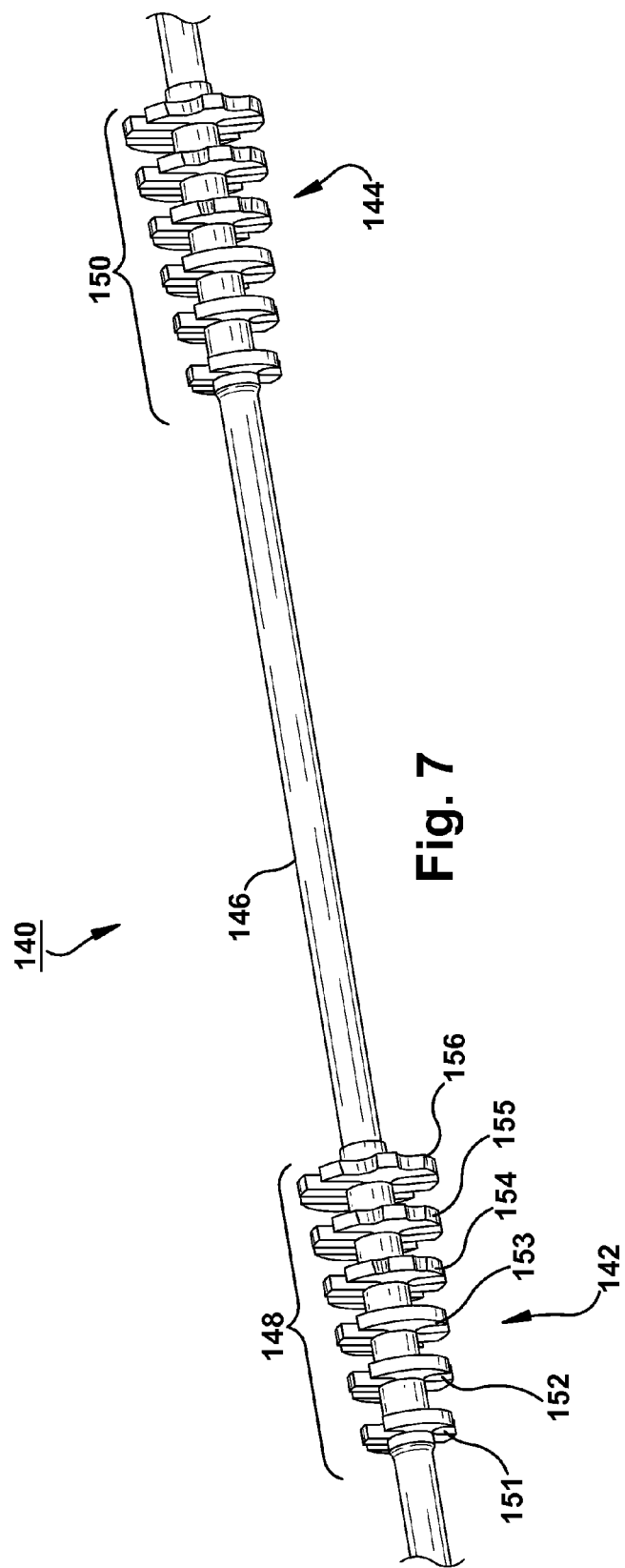
FIG. 7 is a perspective view of another cleaning device, showing two spaced apart squeegee components disposed along a catheter.

Other multiple component cleaning devices may be used in the practice of this invention. For example, FIG. 7 is a perspective view of another cleaning device 140 with two spaced apart squeegee components. A first squeegee 142 and a second squeegee 144 are axially spaced apart along a catheter 146. The first squeegee 142 has a first set of discs 148 and the second squeegee 144 has a second set of discs 150. The two sets 148, 150 may be the same size, shape, and spacing, or they may be different in one or more of those features, in the practice of the invention.

Referring now to the first squeegee 142, the first set of discs 151, 152, 153, 154, 155, 156 are not circular shaped. As discussed, the discs can have any practice shape in the practice of the invention. In this exemplary disc set, the discs increase in cross-sectional area from one side of the squeegee to the other. In other words, one end disc 151 is the smallest disc and an opposing end disc 156 is the largest disc.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some aspects, concepts or features of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, concepts and features may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A cleaning device for use with an endoscope, the device comprising:
    an elongated and flexible base;
    a set of discs axially spaced along the base, each disc positioned along the base at a center point of the disc;
    a brush component, positioned on one side of the set of discs,
    a mechanical barrier, positioned between the set of discs and the brush component, and limiting insertion depth of the cleaning device into an endoscopic device, and
    a ball, positioned at one end of the cleaning device, and preventing from entry of the cleaning device into undersized and undesired channels and ports,
    wherein at least one disc of the set of discs has a circumference which is not equal to a circumference of an adjacent disc of the set of discs.

2. The cleaning device of claim 1, wherein the base is a catheter.

3. The cleaning device of claim 1, wherein the base is a twisted wire.

4. The cleaning device of claim 1, wherein an axial length between any two adjacent discs of the set of discs is less than the maximum radial distance from the base of at least one of the two adjacent discs of the set of discs.

5. The cleaning device of claim 1, wherein at least one disc of the set of discs has a maximum radial distance from the base which is not equal to a maximum radial distance from the base of an adjacent disc of the set of discs.

6. The cleaning device of claim 1, wherein at least one disc of the set of discs has a minimum radial distance from the base which is not equal to a minimum radial distance from the base of an adjacent disc of the set of discs.

7. The cleaning device of claim 1, further comprising a second set of discs axially spaced along the base, each disc of the second set of discs positioned along the base at a center point of the disc, and the second set of discs axially spaced from the first set of discs.

8. A cleaning device for use with an endoscope, the device comprising:
    a catheter;
    a set of discs axially spaced along the catheter, each disc secured to the catheter at a center point of the disc;
    a brush component, positioned on one side of the set of discs,
    a mechanical barrier, positioned between the set of discs and the brush component, and limiting insertion depth of the cleaning device into an endoscopic device, and
    a ball, positioned at one end of the cleaning device, and preventing from entry of the cleaning device into undersized and undesired channels and ports,
    wherein at least one disc of the set of discs has maximum radial distance from the catheter which is greater than an axial distance to an adjacent disc of the set of discs.

9. The cleaning device of claim 8, wherein at least one disc of the set of discs has a circumference which is not equal to a circumference of an adjacent disc of the set of discs.

10. A cleaning device for use with an endoscope, the device comprising:
    a catheter having a proximal end and a distal end;
    a squeegee component secured to the catheter, the squeegee component having a sheath and a set of circular discs axially spaced along the sheath, each disc is positioned on the sheath at a center point of the disc;
    a brush component, positioned on one side of the set of discs,
    a mechanical barrier, positioned between the set of discs and the brush component, and limiting insertion depth of the cleaning device into an endoscopic device, and
    a ball, positioned at one end of the cleaning device, and preventing from entry of the cleaning device into undersized and undesired channels and ports,
    wherein at least one disc of the set of discs has a maximum radial distance from the catheter which is not equal to a maximum radial distance from the catheter of an adjacent disc of the set of discs.

11. The cleaning device of claim 10, wherein an axial length between any two adjacent discs of the set of discs is less than the maximum radial distance from the catheter of at least one of the two adjacent discs of the set of discs.

* * * * *